(12) United States Patent
Goldman

(10) Patent No.: US 11,980,464 B2
(45) Date of Patent: May 14, 2024

(54) COMMUNICATION HEADSET WITH A STRESS MANAGEMENT FUNCTION

(71) Applicant: GN AUDIO A/S, Ballerup (DK)

(72) Inventor: Tomasz Goldman, Ballerup (DK)

(73) Assignee: GN AUDIO A/S, Ballerup (DK)

( * ) Notice: Subject to any disclaimer, the term of this patent is extended or adjusted under 35 U.S.C. 154(b) by 0 days.

(21) Appl. No.: 17/720,906

(22) Filed: Apr. 14, 2022

(65) Prior Publication Data
US 2022/0265185 A1    Aug. 25, 2022

Related U.S. Application Data

(63) Continuation of application No. 15/976,089, filed on May 10, 2018, now abandoned.

(30) Foreign Application Priority Data

May 18, 2017    (EP) .................................... 17171653

(51) Int. Cl.
     *A61B 5/024*      (2006.01)
     *A61B 5/00*      (2006.01)
     (Continued)

(52) U.S. Cl.
     CPC .......... *A61B 5/165* (2013.01); *A61B 5/02405* (2013.01); *A61B 5/02427* (2013.01);
     (Continued)

(58) Field of Classification Search
     CPC . A61B 5/165; A61B 5/02405; A61B 5/02427; A61B 5/02433; A61B 5/02438;
     (Continued)

(56) References Cited

U.S. PATENT DOCUMENTS

| 5,608,794 A | 3/1997 | Larson |
| 7,330,752 B2 | 2/2008 | Kettunen et al. |
| | (Continued) | |

FOREIGN PATENT DOCUMENTS

| KR | 101179943 B1 | 9/2012 |
| KR | 101295046 B1 | 8/2013 |

OTHER PUBLICATIONS

Hjortskov et al. The effect of mental stress on heart rate variability and blood pressure during computer work. Eur J Appl Physiol 92, 84-89 (2004). (Year: 2004).*

(Continued)

*Primary Examiner* — Alex M Valvis
*Assistant Examiner* — Justin Xu
(74) *Attorney, Agent, or Firm* — HSML P.C.

(57) ABSTRACT

Disclosed is a method, a headset and a system for determining heart rate data of a user. The system comprising a headset for voice communication, the headset being configured to be worn at least partly at or in the ear of the user, the headset comprising: a voice communication unit for enabling a voice communication call mode for establishing a call between the headset and a far-end device; a speaker for reproduction of audio signals; a microphone for reception of audio signals; a photoplethysmograph (PPG) sensor for optically measuring through the skin of the user in or at the ear of the user; wherein the system comprises a processing unit connected to the PPG sensor, where the processing unit is configured for determining heart rate data of the user based on the PPG sensor measurements; wherein the system comprises detecting whether the user is on-call with a far-end device or off-call; and wherein the system comprises a data communication unit for providing the determined heart rate data of the user, when the user is wearing the headset, for indication of the heart rate data of the user.

8 Claims, 8 Drawing Sheets

(51) Int. Cl.
*A61B 5/16* (2006.01)
*H04M 1/05* (2006.01)
*H04M 1/21* (2006.01)
*H04R 1/10* (2006.01)

(52) U.S. Cl.
CPC ...... *A61B 5/02433* (2013.01); *A61B 5/02438* (2013.01); *A61B 5/6803* (2013.01); *A61B 5/6817* (2013.01); *A61B 5/721* (2013.01); *A61B 5/7278* (2013.01); *A61B 5/746* (2013.01); *H04M 1/05* (2013.01); *H04M 1/21* (2013.01); *H04R 1/1041* (2013.01); *H04M 2250/12* (2013.01)

(58) Field of Classification Search
CPC ..... A61B 5/6803; A61B 5/6817; A61B 5/721; A61B 5/7278; A61B 5/746; A61B 5/02416; A61B 5/72; H04M 1/05; H04M 1/21; H04M 2250/12; H04R 1/1041; H04R 1/1091
See application file for complete search history.

(56) References Cited

U.S. PATENT DOCUMENTS

| | | | |
|---|---|---|---|
| 7,617,457 | B2 | 11/2009 | Kortum et al. |
| 8,066,637 | B2 | 11/2011 | Childre et al. |
| 8,298,131 | B2 | 10/2012 | Chung et al. |
| 2002/0148470 | A1 | 10/2002 | Blue et al. |
| 2008/0013777 | A1 | 1/2008 | Park et al. |
| 2008/0165017 | A1 | 7/2008 | Schwartz |
| 2008/0177162 | A1 | 7/2008 | Bae et al. |
| 2008/0214903 | A1 | 9/2008 | Orbach |
| 2010/0280338 | A1 | 11/2010 | Chou |
| 2013/0039509 | A1* | 2/2013 | Chuang ................ A61B 5/6814 381/74 |
| 2013/0184517 | A1 | 7/2013 | Collier |
| 2014/0243630 | A1 | 8/2014 | Melker et al. |
| 2014/0243631 | A1 | 8/2014 | Melker |
| 2015/0271329 | A1 | 9/2015 | Deshmukh et al. |
| 2015/0289813 | A1 | 10/2015 | Lipov |
| 2016/0157776 | A1 | 6/2016 | Mestha et al. |
| 2016/0256117 | A1 | 9/2016 | Baik et al. |
| 2017/0100066 | A1 | 4/2017 | Delaney et al. |
| 2017/0181649 | A1 | 6/2017 | Carter et al. |
| 2017/0251295 | A1 | 8/2017 | Pergament et al. |

OTHER PUBLICATIONS

P Madhan Mohan et al., "Stress measurement from wearable photoplethysmographic sensor using heart rate variability data", 2016 International Conference on Communication and Signal Processing (ICCSP), IEEE Xplore, Nov. 24, 2016, cited in Office Action issued in the corresponding European application.
Extended European Search Report for European patent application No. 17171653.3 dated Nov. 7, 2017.
Apple: "Your Heart rate. What it means, and where on Apple Watch you'll find it.—Apple Support", May 16, 2017, XP055418297, retrieved from the Internet: URL:http://web.archive.org/web/20170516023225/https://support.apple.com/en-us/HT204666 [retrieved on Oct. 24, 2017.
Stress and Recovery Analysis Method Based on 24-hour Heart Rate Variability, pp. 1-13, Firstbeat Technologies Ltd., Finland, Published: Sep. 16, 2014, updated: Nov. 4, 2014.
Conference "Biomedical Engineering"; Comparison of green, blue and infrared light in wrist and forehead photoplethysmography; V. Vizbara et al.; Biomedical Engineering Institute, Kaunas University of Technology, Lithuania, pp. 78-81, Jan. 2013.
Multimodal Sensory Headband for Personalized Relaxation Management; Huang et al.; Mar. 3, 2016; http://dl.acm.org/citation.cfm?id=2846723.
The Effects of Emotions on Short-Term Power Spectrum Analysis of Heart Rate Variability, Rollin McCraty et al.; The American Journal of Cardiology, vol. 76 • No. 14 • Nov. 15, 1995 • pp. 1089-1093.
Heart rate variability Standards of measurement, physiological interpretation, and clinical use Task Force of The European Society of Cardiology and The North American Society of Pacing and Electrophysiology (Membership of the Task Force listed in the Appendix), European Society of Cardiology, European Heart Journal, vol. 17, pp. 354-381, Mar. 1996.
Getting started with RHRV, Version 2.0; Constantino A. Garcia et al., pp. 1-149, Jan. 31, 2014.
Heart rate variability: a review; N. Rajendra Acharya et al.; Received: Oct. 19, 2005 / Accepted: Oct. 10, 2006 / Published online: Nov. 17, 2006; International Federation for Medical and Biological Engineering 2006, pp. 1031-1051.
Kubios HRV version 2.2, http://kubios.uef User's Guide, pp. 1-44, Jun. 5, 2014; Mika P. Tarvainen, Ph.D., Biosignal Analysis and Medical Imaging Group, Department of Applied Physics, University of Eastern Finland, Kuopio, Finland.
Wearable Photoplethysmographic Sensors—Past and Present, Toshiyo Tamura et al., Electronics 2014, 3, pp. 282-302; doi: 10.3390/electronics3020282, www.mdpi.com/journal/electronics, Received: Feb. 25, 2014, in revised form: Apr. 15, 2014, Accepted: Apr. 18, 2014, Published: Apr. 23, 2014.
Associations of physical activity, fitness, and body composition with heart rate variability-based Indicators of stress and recovery on workdays: a cross-sectional study; Journal of Occupational Medicine and Toxicology 2014, Teisala et al., pp. 1-9:16. http://www.occup-med.com/content/9/1/16 Received: Feb. 21, 2014, Accepted: Apr. 9, 2014, Published: Apr. 18, 2014.
European patent application 17171653.3 Examination Report from the European Patent Office dated Nov. 25, 2019, 8 pages.
Examination Report issued corresponding European Application No. 17 171 653.3, dated Sep. 14, 2020, 11 pages provided.
Summons to attend oral proceedings issued in European application No. 17 171 653.3, dated Aug. 31, 2021.
Hjortskov et al. The effect of mental stress on heart rate variability and blood pressure during computer work. Eur J Appl Physiol 92, 84-89 (2004). https://doi.org/10.1007/s00421-004-1055-z. (Year: 2004).

* cited by examiner

Optimal position for the fold in the cushion faceplate

COMMUNICATION HEADSET WITH A STRESS MANAGEMENT FUNCTION

FIELD

The present disclosure relates to a method and a system for determining heart rate data of a user. The system comprises a headset for voice communication, and the headset is configured to be worn at least partly at or in the ear of the user.

BACKGROUND

Working in a call center can be very stressful, especially when dealing with customer complaints, problem resolution etc. A stressed call center agent may lose temper or in other ways be perceived as impolite.

Employees working in open plan offices are exposed to noise, and distracting conversations. This generates increased stress level.

Thus there is a need for monitoring, detecting and providing stress feedback to these persons, "in the moment" or as a daily indicator.

SUMMARY

Disclosed is a system for determining heart rate data of a user. The system comprises a headset for voice communication. The headset is configured to be worn at least partly at or in the ear of the user. The headset comprises a voice communication unit for enabling a voice communication call mode for establishing a call between the headset and a far-end device. The headset comprises a speaker for reproduction of audio signals. The headset comprises a microphone for reception of audio signals. The headset comprises a photoplethysmograph (PPG) sensor for optically measuring through the skin of the user in or at the ear of the user. The system comprises a processing unit connected to the PPG sensor. The processing unit is configured for determining heart rate data of the user based on the PPG sensor measurements. The system comprises detecting whether the user is on-call with a far-end device or off-call. The system comprises a data communication unit for providing the determined heart rate data of the user, when the user is wearing the headset, for indication of the heart rate data of the user.

It is an advantage that the determined heart rate data of the user can be used to detect stress of the user. The heart rate data of the user is determined by means of a photoplethysmograph (PPG) sensor. The system comprises a processing unit which is configured for determining heart rate data of the user based on PPG sensor measurements. It is an advantage that the PPG sensor is arranged in the headset configured to be worn by the user. The headset comprises the photoplethysmograph (PPG) sensor for optically measuring through the skin of the user in or at the ear of the user. Thus it is an advantage that the headset comprises the PPG sensor.

When the user of the headset is a call center agent or an employee working in an open plan office, the user will typically wear the voice communication headset for extended periods of a working day, since the user may have many or long phone calls with other persons at far-end devices, and/or since the user may listen to music or use a noise cancellation function in the voice communication headset in order to avoid the noise from the surroundings in the office.

When the user wears the headset, e.g. for extended periods of a working day, it is an advantage that the PPG sensor is arranged in the headset, since then the PPG sensor measurements can be performed when the user is anyway wearing the headset.

Further it is an advantage that the PPG sensor measurements can be used to detect stress of the user over a short time period, e.g. substantially momentarily, such that a specific event, e.g. a specific call conversation with a customer, can be linked or associated with increased stress of the user.

Further it is an advantage that the PPG sensor measurements can be used to detect stress of the user over longer time periods, e.g. a whole day, a week, a month etc., such that increased stress of the user over long terms can be detected.

It is an advantage that the system can detect whether the user is on-call with a far-end device or off-call, since thereby the system can link or associate the determined heart rate data or detected stress with time periods where the user is on-call or off-call.

The system comprises a headset for voice communication, where the voice communication may be via a wireless connection or via a wired connection.

The headset is configured to be worn at least partly at or in the ear of the user. Thus the headset may comprise earcups, where the earcups are of a circumaural design enclosing the ears of the user completely, or where the earcups are of a supra-aural design not completely enclosing the ears of the user. Alternatively the headset may comprise earbuds or earpieces configured to be arranged in the outer part of the ear canal of the user.

The headset comprises a voice communication unit for enabling a voice communication call mode for establishing a call between the headset and a far-end device. The voice communication unit may be a transceiver. Thus the headset is configured for voice communication by establishing phone calls with far-end devices, such as other phones, telephones, cell phones, smartphones, IP phones, Skype calls etc.

The headset comprises a speaker for reproduction of audio signals, thus the speaker transmits the voice or speech from the person in the far-end device to the ears of the user wearing the headset.

The headset comprises a microphone for reception of audio signals, thus the voice or speech from the user of the headset is transmitted through the microphone of the headset to the far-end device.

The system comprises a processing unit connected to the PPG sensor. The processing unit may be arranged in the headset. Alternatively and/or additionally the processing unit may be arranged external from the headset, e.g. in the user's computer, in the supervisor/managers computer etc. The processing unit may be connected to the PPG sensor either wired or wirelessly. If the processing unit is arranged in the headset, the processing unit will typically be connected to the PPG sensor via a wire. If the processing unit is not arranged in the headset, i.e. arranged external from the headset, the processing unit may be connected wirelessly to the PPG sensor.

The processing unit is configured for determining heart rate data of the user based on the PPG sensor measurements, thus the term heart rate data may be used as a general overall expression for what is measured or determined using the PPG sensor. The heart rate data may be processed in various ways in order to detect stress, performing well-being analysis of the user, determining the heart rate (HR) of the user, determining beat-to-beat (RRi) intervals of the user, determining heart rate variability (HRV) of the user etc.

The system comprises detecting whether the user is on-call with a far-end device or off-call. Thus the headset may be in a call mode when the user is on-call, and the headset may be in a non-call mode when the user is off-call. A time period or time interval where the user is off-call may be referred to as a first time interval T1. A time period or time interval where the user is on-call may be referred to as a second time interval T2.

The system comprises a data communication unit for providing the determined heart rate data of the user, when the user is wearing the headset, for indication of the heart rate data of the user. Heart rate data of the user is determined when the user is wearing the headset, since the PPG sensor is arranged in the headset and configured for measuring on/at the skin of the user. Thus heart rate data can only be obtained when the user is wearing the headset. However the data communication unit may provide the determined heart rate data when the user is wearing the headset and/or after the user is finished wearing the headset and/or when the user is taking a break from wearing the headset, such as during a lunch break. The data communication unit is configured for transmitting the data from the processing unit, e.g. in the headset, to for example an external electronic device belonging the user's supervisor or manager, such that the user's supervisor or manager receives the indication of the heart rate data of the user and can act accordingly in case of detected stress in the user etc. The external electronic device belonging to the supervisor or manager may comprise a corresponding data communication unit for receiving the transmitted data from the processing unit.

Indication of the heart rate data of the user may be provided both when the user is on-call and off-call, or only when the user is on-call. Thus the heart rate data may be provided for or during specific time intervals.

Thus it is an advantage to have a body worn device which can monitor and detect stress level and provide a stress feedback to the user, "in the moment" or as a daily indicator. A feedback signal can be provided to the call agent or the supervisor, as a visual or audio signal.

In both situations described above, i.e. a user being a call center agent or an employee working in an open plan office, it is common for the user to wear headsets for extended periods of time. A headset provides an advantageous location for body sensors which can be used to detect stress triggering a feedback to the user nudging the user to rest, or to reduce the workload, or to take a relaxation exercise. Using a photoplethysmograph (PPG) sensor as an on-head detection sensor can be used to detect a lack of physical activity and nudge the user to take a break from work in to relax. Additionally measuring biometrics parameters like Heart Rate (HR), Blood Pressure (BP) and collecting them on a daily basis can provide additional well-being indicators.

Disclosed is a method performed in the system according to the above for determining heart rate data of a user. The method comprises:
- determining a heart rate (HR);
- determining beat-to-beat (RRi) intervals;
- determining a heart rate variability (HRV) during a time interval based on the determined beat-to-beat (RRi) intervals;
- determining low frequency (LF) components and high frequency (HF) components based on the heart rate variability (HRV), where the low frequency (LF) components and the high frequency (HF) components are components in a beat-to beat (RRi) periodogram, where the beat-to beat (RRi) periodogram is based on the determined beat-to beat (RRi) intervals;
- determining a baseline measurement of the low frequency (LF) components and the high frequency (HF) components during a first time interval T1, when the user is off-call, and wherein the processing unit is configured for measuring a first ratio (LF/HF-off call) between the low frequency (LF) components and the high frequency (HF) components during the first time interval T1;
- measuring a second ratio (LF/HF-on call) between the low frequency (LF) components and the high frequency (HF) components during a second time interval T2, when the user is on-call;
- detecting stress by detection of the heart rate exceeding a first predefined threshold value (threshold1) and/or by detection of the second ratio (LF/HF on-call) exceeding a second predefined threshold value (threshold2).

In some embodiments the processing unit is configured for determining the heart rate (HR) and determining beat-to-beat (RRi) intervals based on the PPG sensor measurements, and the processing unit is configured for determining a heart rate variability (HRV) during a time interval based on the beat-to-beat (RRi) intervals.

Heart rate (HR) may be current heart rate. Thus heart rate (HR) may not be over a period of time. However a current heart rate (HR) may be over, e.g. a very short time interval, such as a few seconds, milliseconds etc. Heart rate variability (HRV) may be over a period of time or during a time interval. The heart rate variability (HRV) may be determined solely from the beat-to-beat (RRi) intervals. Beat-to-beat intervals (RRi) may be time intervals between heart beats, where heart beats is a contraction of the heart muscle resulting in a volume of blood being moved. Heart rate variability (HRV) is a broad term covering extraction of many parameters, one of them is the ratio between low frequency and high frequency (LF/HF) which is indicative of stress, as the definition of the stress is that the sympathetic nervous activity dominates the autonomous nervous system.

In some embodiments the processing unit is configured for determining low frequency (LF) components and high frequency (HF) components based on the heart rate variability (HRV), where the low frequency (LF) components and the high frequency (HF) components are components in a beat-to beat (RRi) periodogram, where the beat-to beat (RRi) periodogram is based on the determined beat-to beat (RRi) intervals.

In some embodiments the processing unit is configured for determining a baseline measurement of the low frequency (LF) components and the high frequency (HF) components during a first time interval T1, when the user is off-call, and the processing unit is configured for measuring a first ratio (LF/HF-off call) between the low frequency (LF) components and the high frequency (HF) components during the first time interval T1.

Thus the baseline measurement during the first time interval T1, and i.e. the measurement of the first ratio (LF/HF-off call) is performed when the user is off-call, i.e. not having a call, where it can be assumed that the user is calm and not stressed. The baseline measurement during the first time interval T1 may for example be performed at the start of a working day, such as at the beginning of each working day, or such as each Monday morning, or such as performed after the user has just finished a relaxation exercise etc.

In some embodiments the processing unit is configured for measuring a second ratio (LF/HF-on call) between the low frequency (LF) components and the high frequency (HF) components during a second time interval T2, when the user is on-call.

Thus the measurement of the second ratio (LF/HF-on call) during the second time interval T2 is performed when the user is having a call, since this is a time period where it can happen that the user becomes stressed.

In some embodiments the processing unit is configured to detect stress by detection of the heart rate exceeding a first predefined threshold value (threshold1) and/or by detection of the second ratio (LF/HF on-call) exceeding a second predefined threshold value (threshold2).

Stress can be detected by either (a) the heart rate (HR) exceeding a first predefined threshold value (threshold1) or (b) the ratio LF/HF, determined from the heart rate variability (HRV) analysis, exceeding a second predefined threshold value (threshold2). There may not have to be a heart rate (HR) increase in order to obtain a change in the LF/HF ratio. The heart rate (HR) may increase also due to a mental load, but high heart rate (HR) is indicative of stress too, and will also result in a high blood pressure. Thus the processing unit of the system is configured to detect heart rate (HR) exceeding a first predefined threshold value (threshold1) and/or to detect the second ratio (LF/HF on-call) exceeding a second predefined threshold value (threshold2) to detect stress, in the second time interval T2, when the user is on-call. The detection may be performed throughout the entire second time interval T2 or may be a subset of the second time interval T2. The detected heart rate increase may be an increase exceeding a threshold, and/or a significant heart rate increase, and/or an increase of a certain magnitude etc.

In some embodiments the system comprises a notification unit for providing a notification, if the processing unit detects a heart rate increase of the user. The notification may be to the user and/or to the supervisor or manager. The notification may be an audio, visual and/or tactile notification, such as a warning sound, voice or speech in the headset and/or on an associated computer, a flashing light in the headset and/or on an associated computer, and/or vibration of the headset and/or on an associated computer etc.

In some embodiments the headset comprises a motion sensor configured for detecting head movements of the user for filtering out motion-induced artefacts in the PPG sensor measurements.

In some embodiments the headset is configured such that the PPG sensor is arranged at the preauricular skin pit area of the user for obtaining the PPG signal from the superficial temporary artery, when the user is wearing the headset. The PPG sensor may be arranged at the preauricular skin pit area of the user for example where the headset comprises a circumaural earcup covering or touching the preauricular skin pit area of the user.

In some embodiments the headset is configured such that the PPG sensor is arranged at less than 5 mm over the skin surface, such as less than 4 mm, or such as less than 3 mm, or such as less than 2 mm, or such as less than 1 mm over the skin surface, when the user is wearing the headset. The PPG sensor may be arranged at less than 5 mm over the skin surface for example when the headset comprises a circumaural earcup or when the headset is an in-ear device such as a sport headset.

In some embodiments the headset comprises an earphone housing, and an ear cushion is mounted on the earphone housing, and the PPG sensor is mounted in the earphone housing or in the ear cushion. Hereby it can be achieved that the PPG sensor is arranged at the preauricular skin pit area of the user for obtaining the PPG signal from the superficial temporary artery, when the user is wearing the headset.

In some embodiments the earphone housing comprises a protrusion where the PPG sensor is configured to be arranged, such that the protrusion is configured to rest/be situated at the preauricular skin pit area of the user, when the user is wearing the headset. The protrusion may be an angled part, a raised part, a bend etc. For example, the earphone housing may comprise a first face configured to point towards the ear/skin of the user when the user is wearing the headset. The earphone housing may comprise a second face configured to point towards the surroundings when user is wearing the headset. The protrusion may be arranged in the first face. The protrusion may be an angled part having an angle relative to a plane, e.g. the plane of the second face, of between 10 degrees and 60 degrees. The protrusion or angled part may be arranged at a centreline of the earphone housing, or arranged skew/oblique relative to a centreline of the earphone housing.

In some embodiments the headset comprises a fixation part for fixing the position of the earphone housing, when the user is wearing the headset, such that the PPG sensor is arranged at the preauricular skin pit area of the user. The fixation part may be a bar, or a rod from a headband part of the headset to fixate or keep the earcup part at the ear for ensuring that the PPG sensor is arranged at the preauricular skin pit area of the user.

In some embodiments the system comprises an on-call indicator for indicating if the headset is in a call mode or in a non-call mode for detecting whether the user is on-call with a far-end device or off-call.

Thus the system comprises detecting whether the user is on-call with a far-end device or off-call. The system may perform this detection by detecting whether the headset is in a call mode or in a non-call mode. The system, e.g. the headset, may comprise an on-call indicator for indicating or detecting whether the headset is in a call mode, i.e. on-call, or in a non-call mode, i.e. off-call.

It is an advantage that the system can detect whether the user is on-call with a far-end device or off-call, since thereby the system can link or associate the determined heart rate data or detected stress with time periods where the user is on-call or off-call.

Disclosed is a headset configured for voice communication, where the headset is configured to be worn at least partly at or in the ear of a user, where the headset is configured for use in a system according to the above.

The headset may be a USB-connected wired communication headset with a PPG sensor. The PPG sensor is configured to be connected to a processor (DSP) controlling sampling of PPG data. The PPG sensor and its processor are configured to determine heart rate (HR) and beat-to-beat (Ri-R)i intervals, and perform Heart Rate Variability (HRV) analysis. Based on HRV analysis the LF (low frequency) and HF (high frequency) components in an RRi periodogram are configured to be determined, detecting periods of stress both when the user is on call and when not on call. The system may be configured to provide audio and/or visual feedback to the user to influence the user's behavior. Based on sensor feedback the user may have the possibility to request a "relaxation service" (de-stress service), for example by the headset being configured to connect to an app or a web service providing a relaxation coaching by means of audio coaching, e.g. a combination of music and breathing exercises. Alternatively and/or additionally the headset and/or the system may be configured for providing a visual and/or audio feedback based on real-time analysis of HRV which is affected by the breathing.

The PPG sensor may additionally be used as a reliable detector of whether the headset is mounted on the user's head. Therefore the PPG sensor can be configured to be used to detect when the user is sitting at work i.e. detecting periods of low/none physical activity.

The combination of one or more of stress index, HR, at-work-indicator, on-call indicator etc. are configured to be collected and logged during working hours for well-being analysis of the user, e.g. detecting day-to-day changes, impact of workload on the collected biometric data, etc.

The PPG sensor may be configured to be mounted on the user's head to have an unobstructed field of view pointing towards the pre-auricular skin pit thus obtaining the PPG signal from the superficial temporal artery of the user.

The earphone housing in which the PPG sensor and ear cushions are configured to be mounted may be angled or folded or bended allowing for a reasonably precise location of the PPG sensor relative to the pinna and the pre-auricular skin pit of the user.

The system comprises a headset with an embedded photoplethysmographic (PPG) sensor. The headset is configured to be worn by a user. The PPG sensor is connected to a processor, e.g. a DSP (digital signal processor) or the like. The processor is configured for performing an analysis of the heart rate variability of the user, extracting features from the heart rate variability data, estimating a stress metric and may provide near instantaneous feedback to the user or to a supervisor when stress or anger exceeds a threshold.

The reflection PPG sensor is configured to be arranged in proximity to the skin or in contact with the skin of the user, e.g. by being attached to the body. The PPG sensor is configured to use an LED (light emitting diode) light source generating blue (465 nm) and/or green (520 nm) and/or infrared (940 nm) light and/or a combination of lights of multiple wavelengths. A photodetector in the PPG sensor is configured to measure the intensity of the reflected light from the skin/tissue/blood of the user. Due to the absorption of light in blood the reflected light is inversely proportional to the blood volume in the line of sight and can thus be used to track the pulsation of arterial blood.

The mounting or provision of the PPG sensor in the headset may be provided by that the earcup of the headset is of a circumaural design. Headphones which are circumaural, literally meaning "around the ears" may allow for the users ears to be fully enclosed by the earcup. In case of circumaural design the preauricular skin pit area of the user may be a suitable place to measure the PPG signal. The PPG sensor may in such case be embedded in the ear cushion material, which is typically polyurethane or polyester foam. The ear cushion material may be configured such that is it exposing the optical sensor in the PPG such that the optical sensor can be in contact with or close to skin, such within 1-4 mm from the surface of the skin.

The ear cushion with a PPG sensor may be an option in a modular design where the user may choose between ear cushion with or without a PPG sensor.

The earcup may be of a supra-aural design. Supra-aural headphones are headphones that rest on the ear, but does not completely cover, enclose or envelope over the ear. For securing skin or near skin contact with the PPG sensor in the concha a spring loaded arm comprising the PPG sensor may be provided on the earcup. Alternatively, the PPG sensor may be mounted on a PCB (printed circuit board) behind the cushion, and the cushion may have an opening to allow the PPG sensor to have an unobstructed field of view to the skin. The PPG sensor may alternatively be integrated into the earphone housing used to mount the cushion.

Alternatively, the PPG sensor may be embedded in an ear bud type of headsets where the PPG sensor will have a contact with a concha. Jabra Pulse Sport is an example implementation of an ear bud type of headset.

Alternatively, an angled, folded or bended earphone housing may be provided in the earcups of the headset, and may provide a proper location of the PPG sensor at the preauricular skin pit area of the user for obtaining the PPG signal from the superficial temporal artery of the user.

A motion sensor provided in the headset may be used to monitor motion of the user, e.g. when the user is performing physical activity, in order to exclude periods of high physical activity from the stress analysis and to prevent using rather a poor PPG signal during motion as motion will induce artifacts in the PPG signal.

Furthermore, the PPG sensor can be used as a reliable detector of whether the headset is mounted on the user's head or not. If there is no detected PPG signal, the headset is probably not worn by the user. Thus if no PPG signal is detected this is indicative of the headset not being mounted on the user's head. If a PPG signal is detected, this is indicative of the headset is mounted on the user's head.

For detecting stress of the user and/or providing a well-being analysis, the following method may be performed.

Detecting and signaling stress during a call may be provided. In order to truly detect a stress period from non-stress period of the user a baseline measurement may be provided. The processor of the communication headset may know the call context, such as on call, not on call etc.

Thus the processor of the communication headset may be configured to know when the user is on-call. Therefore the processor may be configured to perform the baseline measurement when the user is not on call, and the processor may be configured to measure HRV during a non-call period and during a call. The processor of the communication headset may therefore be configured to detect a change in stress or anger situation and provide a feedback, e.g. intervention, to the user and/or manager and thus provide feedback influencing the user to relax such as to restrain himself or herself. The feedback to the user can be visual or by means of an audio signal provided to the user in the headphones.

A number of thresholds may be used in the analysis:
 t1—absolute LF/HF stress threshold.
 t2—duration when LF/HF>t1 is considered a true stress situation.
 TB1—stress threshold relative to a baseline situation (e.g. at the start of a work day).
 TB2—duration when LF/HF>TB1 is considered a true on-the-spot stress situation.

There are different ways of implementing the signal analysis and data collection and intervention.

The headset can be USB wired or wireless. The signal processing, analysis and intervention may be performed in or through the headset. The resulting HR, HRV and stress metrics may be delivered via a Bluetooth connection or Bluetooth Low Energy connection to a Health app in a smartphone or on a tablet or PC. The resulting HR, HRV and stress metric may be delivered via USB to a connected PC or tablet. Alternatively and/or additionally, the signal processing analysis and intervention may be performed outside the headset, such as in an external processor and/or using an app in a smartphone or in a connected PC or tablet.

The headset may be configured to provide a relaxation exercise, whereby the user may be guided by audio provided in a headset to perform e.g. deep breathing until the processor detects that the user reaches a relaxation state. The relaxation coaching may be provided in an app, such as a smartphone app, or as a web service where the user via the headset connects to a web service which generates audio coaching in response to HR, HRV and stress metrics.

Signal Processing of PPG Signal

The PPG signal may be sampled at a suitable high frequency, typically 250 HZ-1000 Hz to enable millisecond accuracy of the PPG curve and hence a good accuracy of the RR intervals.

The heart rate variability HRV is the variation in beat-to-beat intervals.

A typical analysis process may include:

The PPG curve may be corrected for possible artifacts. The R-R intervals (RRi) are determined from the peaks in the PPG curve. A linear interpolation may be used to transform RRi tachogram into equidistantly spaced samples (resampling).

Different metrics may be used to separate stress periods from "relaxation" periods.

When the sympathetic nervous activity dominates the autonomous nervous system ANS then the subject or user is stressed, as per definition of stress. The parasympathetic nervous activity dominates in the recovery periods. The RR intervals are modulated by those two activities and they can be estimated by performing a Fourier analysis of the RRi resampled data. The separate rhythmic contributions from sympathetic and parasympathetic nervous systems modulate the heart rate intervals RR: the sympathetic activity is associated with low frequencies 0.04-0.15 Hz, while the parasympathetic activity is associated with higher frequency range 0.15-0.4 Hz.

There are potentially many metrics used to evaluate RRi data including graphical Poincare plots.

The low frequency to high frequency ratio is one of the metrics that may be used to detect stress or anger.

The impact of stress can be seen by the LF component (corresponding to the sympathetic nervous system) dominating the frequency spectrum when the subject or user is stressed.

The analysis may use disjoint intervals of fairly short length of 1-4 seconds, longer disjoint intervals or sliding window intervals.

Accordingly it is possible to detect stress or anger both "in the moment" and compute an index for a work day or longer periods.

HRV may be dependent on the extrinsic regulation of the heart rate (HR).

HRV may be a useful signal to understand the status of autonomous nervous system (ANS).

The ANS have sympathetic and parasympathetic components. Sympathetic stimulation is a response to stress, parasympathetic is driven by function of internal organs.

The separate rhythmic contributions from sympathetic and parasympathetic modulate the heart rate intervals RR: sympathetic activity is associated with low frequencies 0.04-0.15 Hz, parasympathetic is associated with higher frequency range 0.15-0.4 Hz.

Numerous analysis methods may be used: time domain (standard deviation of RR intervals SDNN, standard deviation of differences between intervals SDSD, etc.), Poincare geometry analysis, Frequency domain analysis, nonlinear methods, etc.

Stress may be defined as "increased activation level of the body when sympathetic activity dominates the ANS and parasympathetic (vagal) activation is low". Recovery is defined as "reduced activation level of the body when parasympathetic (vagal) activation dominates the ANS over sympathetic activity".

HFP and LFP, obtained typically by Fourier transform from equidistantly resampled RR signal, can be used to distinguish between periods of stress and recovery.

The present invention relates to different aspects including the system described above and in the following, and corresponding system parts, headsets, methods, devices, systems, networks, kits, uses and/or product means, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
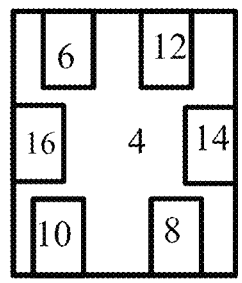
FIG. 1 schematically illustrates an example of a system 2 for determining heart rate data of a user.
Figure 1:
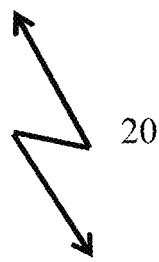
Figure 1:
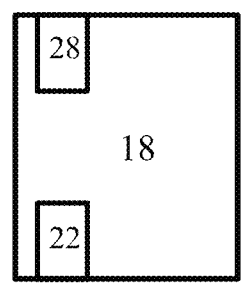

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

FIG. 1 schematically illustrates an example of a system 2 for determining heart rate data of a user. The system 2 comprises a headset 4 for voice communication. The headset 4 is configured to be worn at least partly at or in the ear of the user. The headset 2 comprises a voice communication unit 6 for enabling a voice communication call mode for establishing a call between the headset 4 and a far-end device (not shown). The headset 2 comprises a speaker 8 for reproduction of audio signals. The headset 2 comprises a microphone 10 for reception of audio signals. The headset 2 comprises a photoplethysmograph (PPG) sensor 12 for optically measuring through the skin of the user in or at the ear of the user.

The system 2 comprises a processing unit 14 connected to the PPG sensor 12, where the processing unit 14 is configured for determining heart rate data of the user based on the PPG sensor measurements. In FIG. 1 the processing unit 14 is shown in the headset 2. However the processing unit 14 may alternatively and/or additionally be arranged in an external device 18 external from the headset, e.g. in the user's computer, and/or in a computer belonging or being controlled by a supervisor/manager to the user.

The system 2 comprises detecting whether the user is on-call with a far-end device or off-call.

The system 2 comprises a data communication unit 16 for providing the determined heart rate data of the user, when the user is wearing the headset 4, for indication of the heart rate data of the user. In FIG. 1 the data communication unit 16 is shown to be provided in the headset 2. However if the processing unit 14 is arranged in the external device 18 external from the headset 2, the data communication unit 16 may also be arranged in the external device 18, such as in user's computer, in the supervisor/managers computer etc.

The communication 20 between the headset 2 and the external device 18 may be via a wired connection or via a wireless connection, such as Bluetooth. The external device 18 may comprise a data communication unit 22 for data communication with the data communication unit 16 in headset 2.

The external device 18 may further comprise a display 28 for displaying heart rate data of the user.

Figure 2:
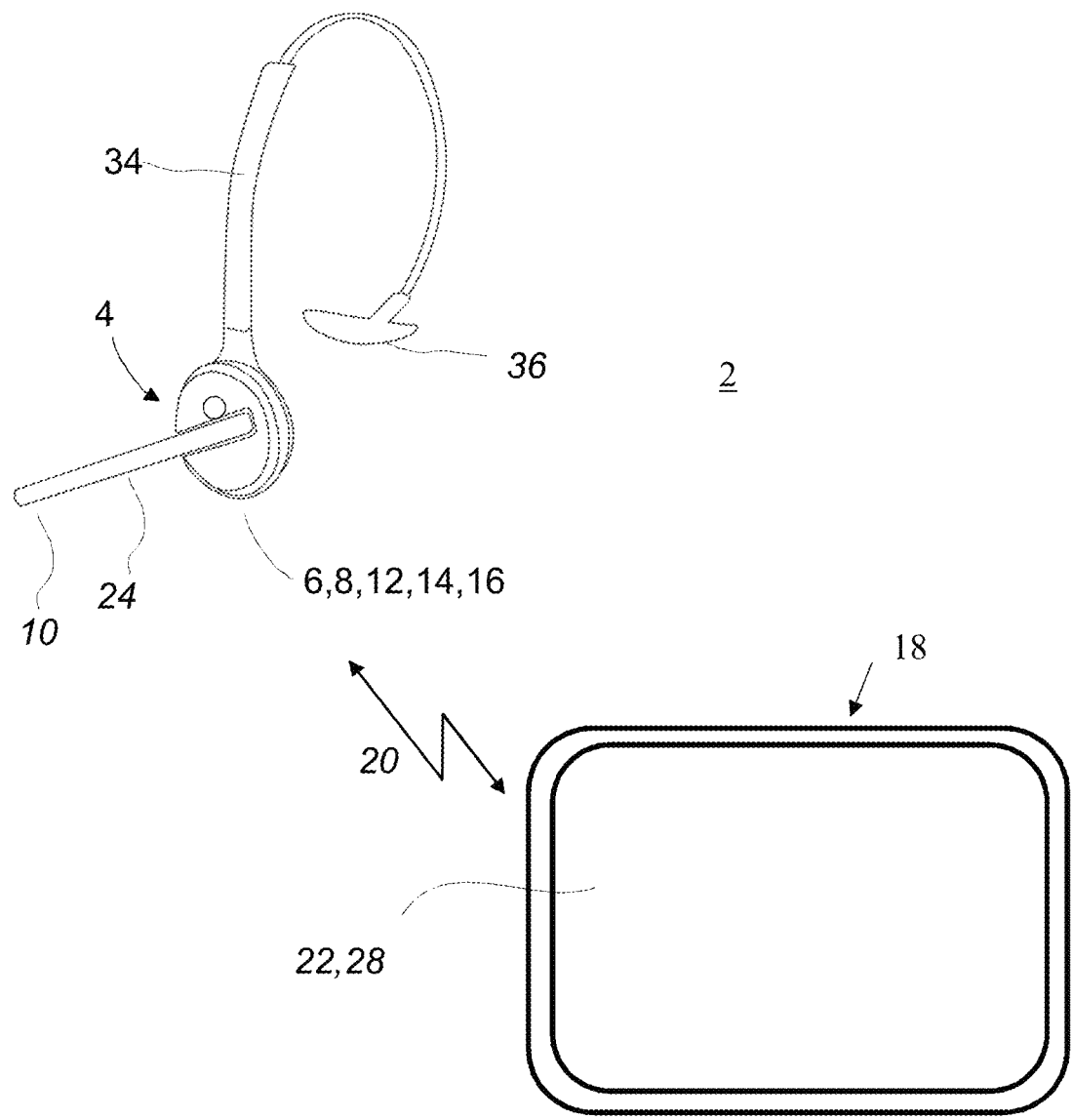
FIG. 2 schematically illustrates an example of a system 2 for determining heart rate data of a user.

FIG. 2 schematically illustrates an example of a system 2 for determining heart rate data of a user. The system 2 comprises a headset 4 for voice communication. The headset 4 is configured to be worn at least partly at or in the ear of the user. The headset 2 comprises a voice communication unit 6 for enabling a voice communication call mode for establishing a call between the headset 4 and a far-end device (not shown). The headset 2 comprises a speaker 8 for reproduction of audio signals. The headset 2 comprises a microphone 10 for reception of audio signals. The headset 2 comprises a photoplethysmograph (PPG) sensor 12 for optically measuring through the skin of the user in or at the ear of the user.

The system 2 comprises a processing unit 14 connected to the PPG sensor 12, where the processing unit 14 is configured for determining heart rate data of the user based on the PPG sensor measurements. In FIG. 2 the processing unit 14 is shown in the headset 2. However the processing unit 14 may alternatively and/or additionally be arranged in an external device 18 external from the headset, e.g. in the user's computer, and/or in a computer belonging or being controlled by a supervisor/manager to the user.

The system 2 comprises detecting whether the user is on-call with a far-end device or off-call.

The system 2 comprises a data communication unit 16 for providing the determined heart rate data of the user, when the user is wearing the headset 4, for indication of the heart rate data of the user. In FIG. 1 the data communication unit 16 is shown to be provided in the headset 2. However if the processing unit 14 is arranged in the external device 18 external from the headset 2, the data communication unit 16 may also be arranged in the external device 18, such as in user's computer, in the supervisor/managers computer etc.

The communication 20 between the headset 2 and the external device 18 may be via a wired connection or via a wireless connection, such as Bluetooth. The external device 18 may comprise a data communication unit 22 for data communication with the data communication unit 16 in headset 2.

The external device 18 may further comprise a display 28 for displaying heart date data of the user.

FIG. 2 further shows that the headset may comprise a microphone boom 24 comprising the microphone 10. The headset may also comprise a headband 34 or neckband for attaching the headset 2 to the head of the user. The shown headset 2 in FIG. 2 is a headset with only one earcup and thus one speaker 8 to cover one ear. The headset 2 is configured to attach to the head of the user at the part 36. Alternatively, the headset 2 may comprise one earbud, or two earcups or two earbuds.

Figure 3:
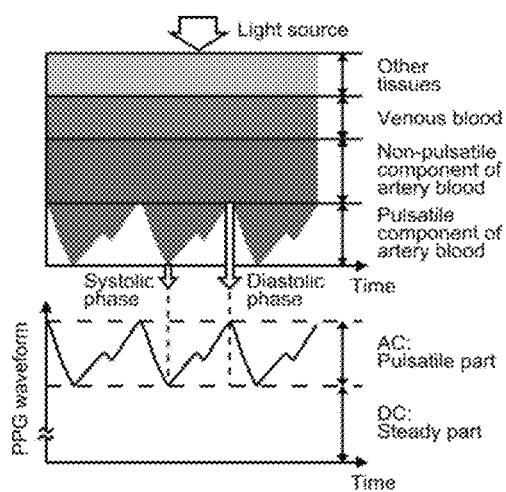
FIG. 3 schematically illustrates a photoplethysmograph (PPG) sensor optically measuring through the skin of the user.

FIG. 3 schematically illustrates a photoplethysmograph (PPG) sensor optically measuring through the skin of the user.

The reflection PPG sensor is configured to be arranged in proximity to the skin or in contact with the skin of the user, e.g. by being attached to the body. The PPG sensor is configured to use an LED (light emitting diode) light source generating blue (465 nm) and/or green (520 nm) and/or infrared (940 nm) light and/or a combination of lights of multiple wavelengths. A photodetector in the PPG sensor is configured to measure the intensity of the reflected light from the skin/tissue/blood of the user. Due to the absorption of light in blood the reflected light is inversely proportional to the blood volume in the line of sight and can thus be used to track the pulsation of arterial blood.

FIG. 3 schematically illustrates that the light source transmits and reflects through tissues, venous blood, the non-pulsatile component of artery blood and the pulsatile component of artery blood, see top part of FIG. 3. The bottom part of FIG. 3 schematically illustrates that the intensity of the reflected light is configured to be measured by the photodetector in the PPG sensor during a time interval (x-axis is time). Due to the absorption of light in blood the reflected light is inversely proportional to the blood volume in the line of sight and can thus be used to track the pulsation of arterial blood.

Figure 4:
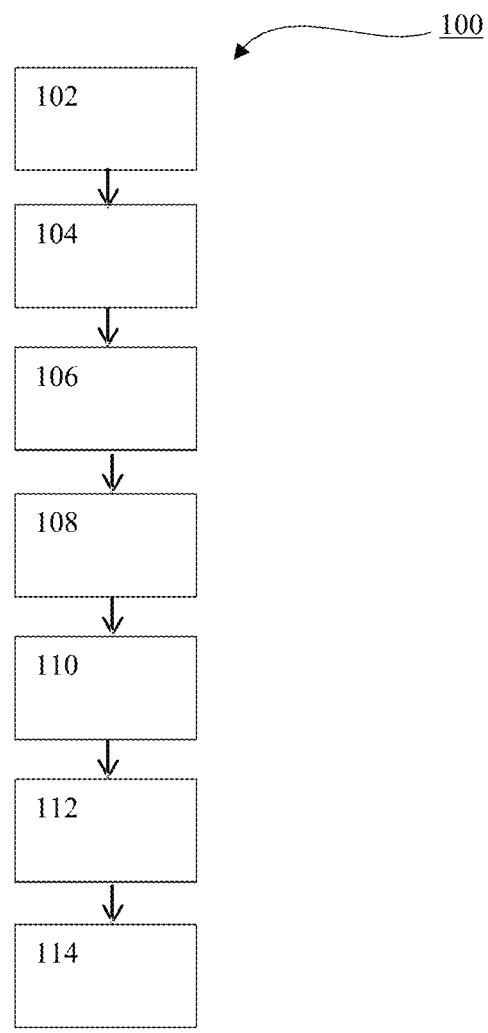
FIG. 4 schematically illustrates a method performed in a system for determining heart rate data of a user.

FIG. 4 schematically illustrates a method 100 performed in a system 2 for determining heart rate data of a user. The method comprises the following steps:

In step 102 a heart rate (HR) of the user is determined.

In step 104 beat-to-beat (RRi) intervals of the user is determined.

In step 106 a heart rate variability (HRV) of the user is determined during a time interval, where the determination 106 is based on the determined beat-to-beat (RRi) intervals from step 104.

In step 108 low frequency (LF) components and high frequency (HF) components are determined based on the heart rate variability (HRV) from step 106, where the low frequency (LF) components and the high frequency (HF) components are components in a beat-to beat (RRi) periodogram, where the beat-to beat (RRi) periodogram is based on the determined beat-to beat (RRi) intervals from step 104.

In step 110 a baseline measurement of the low frequency (LF) components and the high frequency (HF) components is determined during a first time interval T1, when the user is off-call, and the processing unit is configured for measuring a first ratio (LF/HF-off call) between the low frequency (LF) components and the high frequency (HF) components during the first time interval T1.

In step 112 a second ratio (LF/HF-on call) between the low frequency (LF) components and the high frequency (HF) components is measured during a second time interval T2, when the user is on-call.

In step 114 stress is detected by detection of the heart rate exceeding a first predefined threshold value (threshold1) and/or by detection of the second ratio (LF/HF on-call) exceeding a second predefined threshold value (threshold2).

Figure 5:
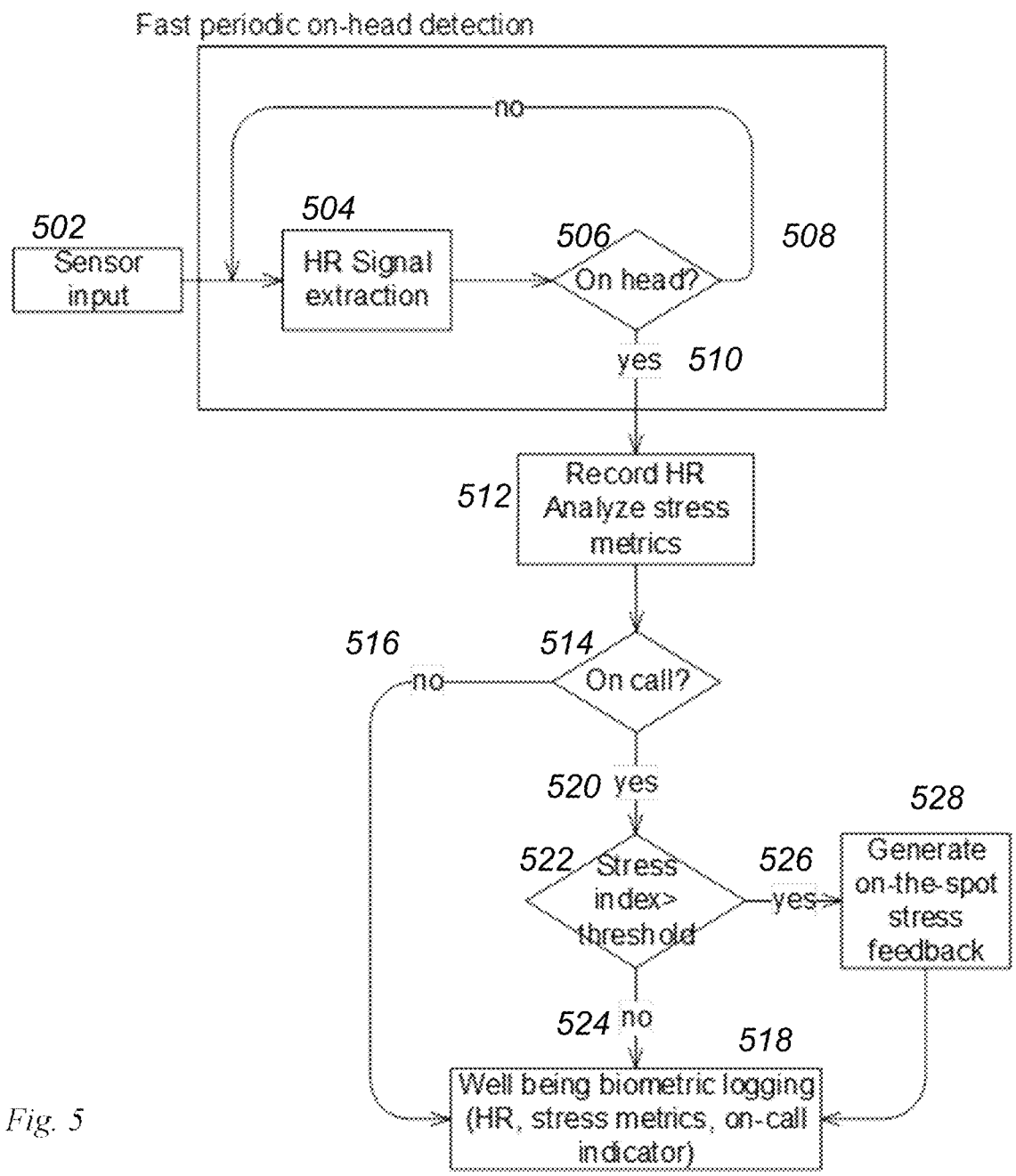
FIG. 5 schematically illustrates a method for a well-being analysis, such as detecting stress of a user, wearing a headset comprising a PPG sensor.

FIG. 5 schematically illustrates a method for a well-being analysis, such as detecting stress of a user, wearing a headset comprising a PPG sensor.

For detecting stress of the user and/or providing a well-being analysis, the following method may be performed.

Detecting and signaling stress during a call may be provided. In order to truly detect a stress period from non-stress period of the user a baseline measurement may be provided. The processor of the communication headset may know the call context, such as on call, not on call etc.

Thus the processor of the communication headset may be configured to know when the user is on-call. Therefore the processor may be configured to perform the baseline measurement when the user is not on call, and the processor may be configured to measure HRV during a non-call period and during a call. The processor of the communication headset may therefore be configured to detect a change in stress or anger situation and provide a feedback, e.g. intervention, to the user and/or manager and thus provide feedback influencing the user to relax such as to restrain himself or herself. The feedback to the user can be visual or by means of an audio signal provided to the user in the headphones.

In FIG. 5 the method comprises transmitting the PPG sensor input 502 to a heart rate (HR) signal extraction 504. The system or the headset detects 506 if the headset is on the user's head. If the headset is not, 508, on the user's head, return to PPG sensor input 502 and HR signal extraction 504. If the headset is on, 510, the user's head, continue to record heart rate (HR) for analyzing stress metrics 512. Then determine 514 if the user in on-call or off-call. If the user is not on-call, 516, then continue to well-being biometric logging (heart rate, stress metrics, on-call detector) 518. If the user is on-call, 520, then continue to determine 522 if stress index exceeds a threshold. If stress index does not exceed a threshold 524, continue to well-being biometric logging (heart rate, stress metrics, on-call detector) 518. If stress index does exceed a threshold 526, then generate on-the-spot stress feedback 528 to the user and continue to well-being biometric logging (heart rate, stress metrics, on-call detector) 518.

Figure 6:
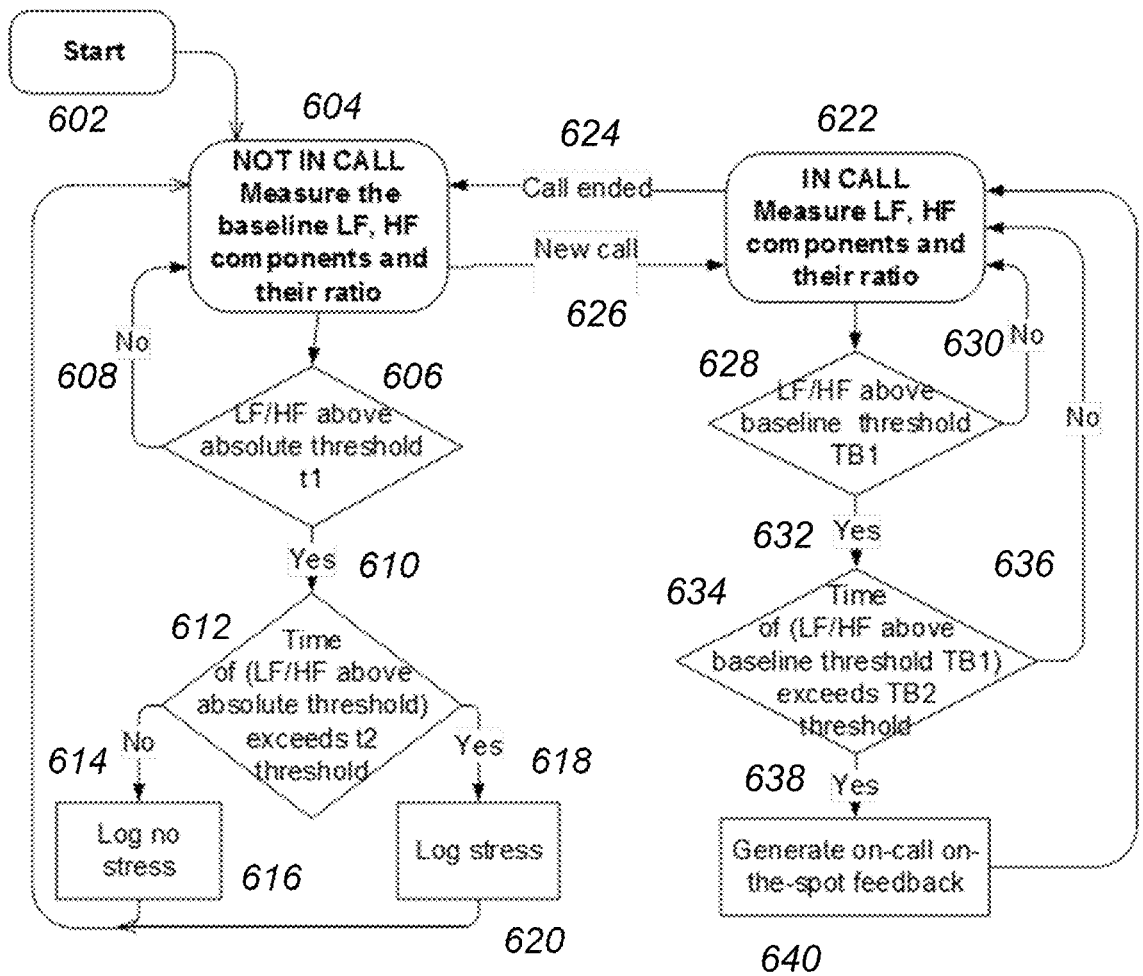
FIG. 6 schematically illustrates a method for a well-being analysis, such as detecting stress of a user, wearing a headset comprising a PPG sensor.

FIG. 6 schematically illustrates a method for a well-being analysis, such as detecting stress of a user, wearing a headset comprising a PPG sensor.

In FIG. 6 a number of thresholds are used:
t1—absolute LF/HF stress threshold.
t2—duration when LF/HF>t1 is considered a true stress situation.
TB1—stress threshold relative to a baseline situation, e.g. at the start of a work day.
TB2—duration when LF/HF>TB1 is considered a true on-the-spot stress situation.

There are different ways of implementing the signal analysis and data collection and intervention.

The headset can be USB wired or wireless. The signal processing, analysis and intervention may be performed in or through the headset. The resulting HR, HRV and stress metrics may be delivered via a Bluetooth connection or Bluetooth Low Energy connection to a Health app in a smartphone or on a tablet or PC. The resulting HR, HRV and stress metric may be delivered via USB to a connected PC or tablet. Alternatively and/or additionally, the signal processing analysis and intervention may be performed outside the headset, such as in an external processor and/or using an app in a smartphone or in a connected PC or tablet.

In FIG. 6 the method comprises starting 602 when the user is not in call 604, i.e. off-call. Here the baseline LF, HF components and their ratio are measured. Then it is determined 606 if the LF/HF is above the absolute threshold t1. If the LF/HF is not, 608, above the absolute threshold t1, then return to the state where the user is not in call 604, i.e. off-call, where the baseline LF, HF components and their ratio are measured. If the LF/HF is above the absolute threshold t1, 610, then continue to determine 612 if the time of (LF/HF above the absolute threshold) exceeds the t2 threshold. If the time of (LF/HF above the absolute threshold) does not, 614, exceed the t2 threshold, then log no stress, 616, and return to the state where the user is not in call 604, i.e. off-call, where the baseline LF, HF components and their ratio are measured. If the time of (LF/HF above the absolute threshold) exceeds, 618, the t2 threshold, then log stress 620, and return to the state where the user is not in call 604, i.e. off-call, where the baseline LF, HF components and their ratio are measured.

For the case where the user is in-call 622, the LF, HF components and their ratio are measured. The change between the user being not in call 604 and the user being in call 622 may be due to either a call is ended 624 or that a new call 626 has begun. When the user is in call 622, it is determined 628, if the LF/HF is above the baseline threshold TB1. If the LF/HF is not, 630, above the baseline threshold TB1, then return to the state where user is in-call 622, where the LF, HF components and their ratio are measured. If the LF/HF is, 632, above the baseline threshold TB1, then determine 634 if the time of (LF/HF above baseline threshold TB1) exceeds TB2 threshold. If the time of (LF/HF above baseline threshold TB1) does not, 636, exceed TB2 threshold, then return to the state where user is in-call 622, where the LF, HF components and their ratio are measured. If the time of (LF/HF above baseline threshold TB1) exceeds, 638, TB2 threshold, then generate on-call on-the-spot feedback 640, and then return to the state where user is in-call 622, where the LF, HF components and their ratio are measured.

Figure 7:
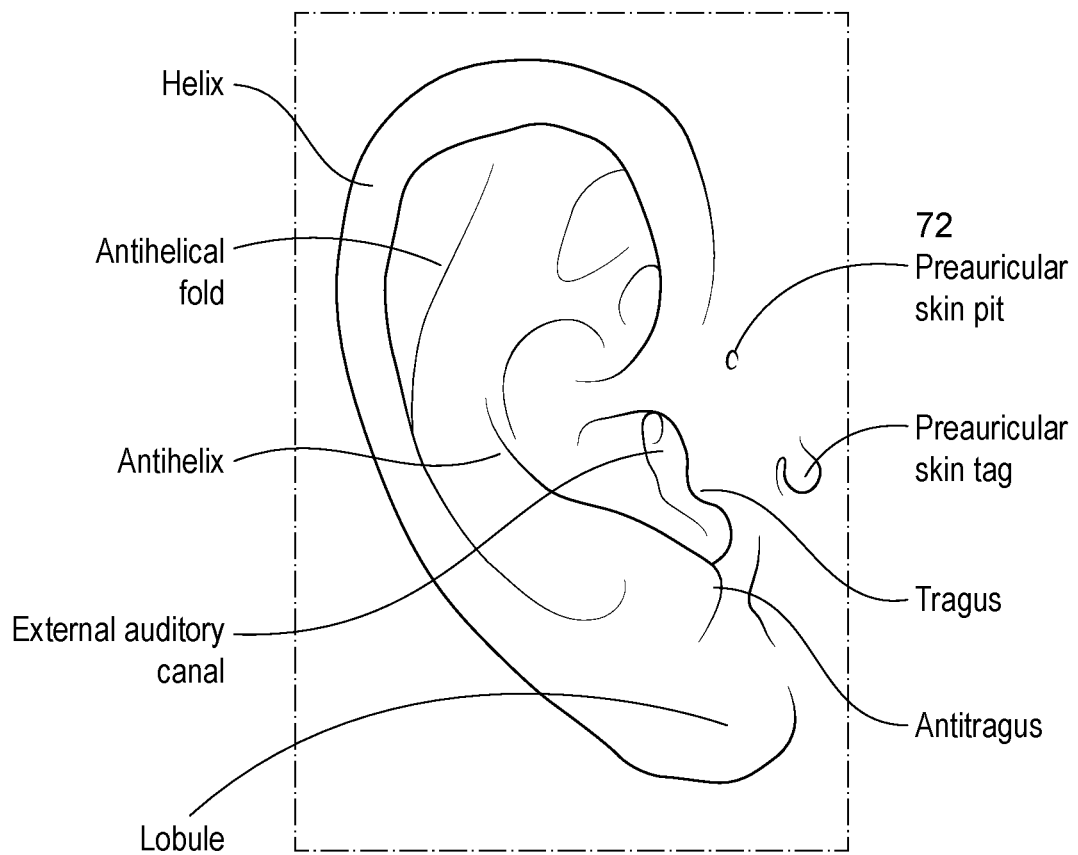
FIG. 7 schematically illustrates the anatomy of the outer ear showing the approximate position of the preauricular skin pit.

FIG. 7 schematically illustrates the anatomy of the outer ear showing the approximate position of the preauricular skin pit 72. The PPG sensor in the headset is configured to be arranged at the preauricular skin pit area of the user for obtaining the PPG signal from the superficial temporary artery, when the user is wearing the headset.

Figure 8A:
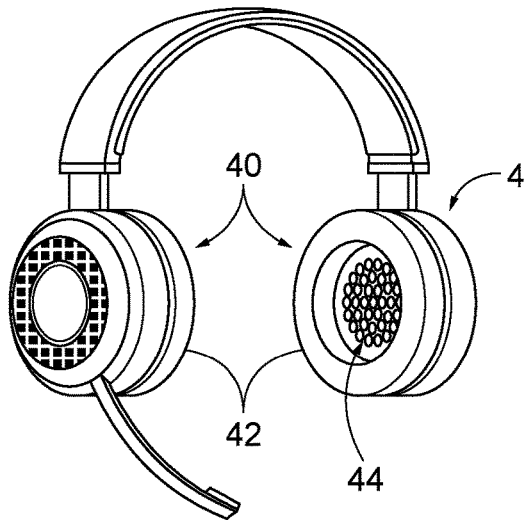
FIGS. 8A-8B schematically illustrate a headset with a PPG sensor and an earcup of the headset with a circumaural design.
Figure 8B:
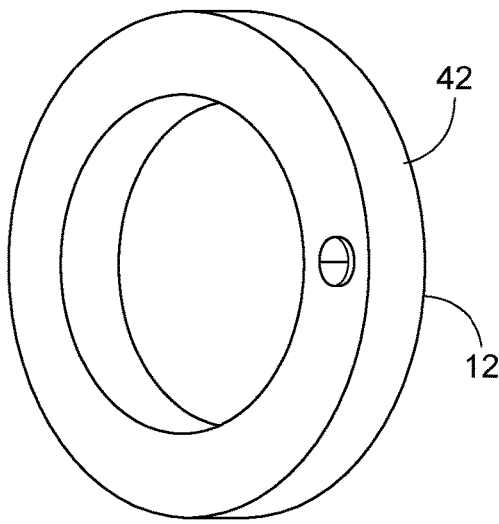

FIGS. 8A-8B schematically illustrate a headset with a PPG sensor and an earcup of the headset with a circumaural design.

The mounting or provision of the PPG sensor 12 in the headset 4 may be provided by that the earcup 40 of the headset 4 is of a circumaural design, see FIG. 8A. The earcup 40 comprises an earphone housing 44 and an ear cushion material 42. In case of a circumaural design, the preauricular skin pit area of the user may be a suitable place to measure the PPG signal. FIG. 8B shows that the PPG sensor 12 may in such case be embedded in the ear cushion material 42, which is typically polyurethane or polyester foam. The ear cushion material 42 may be configured such that is it exposing the optical sensor in the PPG 12 such that the optical sensor can be in contact with or close to skin, such within 1-4 mm from the surface of the skin.

Figure 9A:
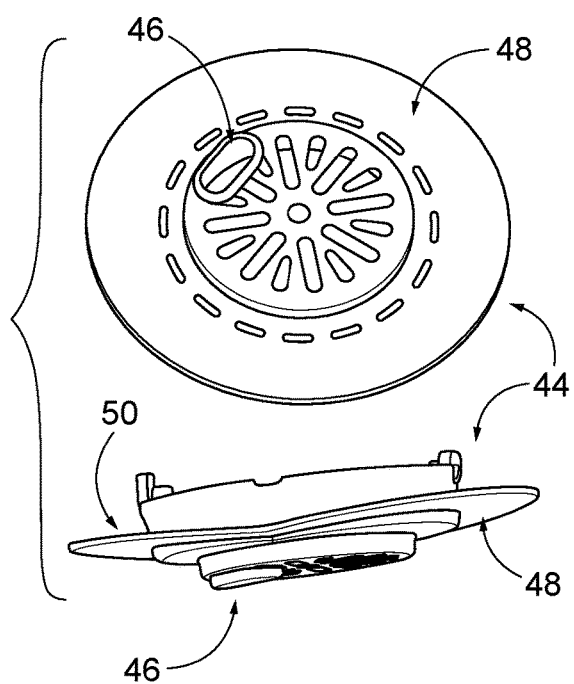
FIG. 9A schematically illustrates an angled earphone housing, comprising a protrusion, provided in the earcups of the headset.

FIG. 9A schematically illustrates an angled, folded or bended earphone housing 44 provided in the earcups 40, see FIG. 8, of the headset. The angled, folded or bended earphone housing 44 may provide a proper location of the PPG sensor at the preauricular skin pit area of the user for obtaining the PPG signal from the superficial temporal artery of the user.

The earphone housing 44 comprise a protrusion 46 where the PPG sensor is configured to be arranged, such that the protrusion is configured to rest/be situated at the preauricular skin pit area of the user, when the user is wearing the headset. The protrusion 46 may be an angled part, a raised part, a bend etc. For example, the earphone housing 44 may comprise a first face 48 configured to point towards the ear/skin of the user when the user is wearing the headset. The earphone housing 44 may comprise a second face 50 configured to point towards the surroundings when user is wearing the headset. The protrusion 46 may be arranged in the first face 48. The protrusion 46 may be an angled part having an angle relative to a plane, e.g. the plane of the second face 50, of between 10 degrees and 60 degrees. The protrusion 46 or angled part may be arranged at a centreline of the earphone housing 44, or arranged skew/oblique relative to a centreline of the earphone housing 44.

Figure 9B:
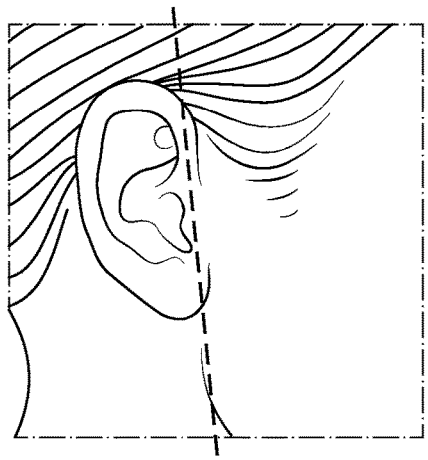
FIG. 9B illustrates with the dotted line the optimal position for the protrusion or angled part of the earphone housing, see FIG. 9A.

FIG. 9B illustrates with the dotted line the optimal position for the protrusion or angled part of the earphone housing, see FIG. 9A.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications and equivalents.

LIST OF REFERENCES 2 system
4 headset
6 voice communication unit of headset
8 speaker of headset
10 microphone of headset
12 photoplethysmograph (PPG) sensor
14 processing unit
16 data communication unit
18 external device
20 communication between headset and external device
22 data communication unit of external device
24 microphone boom of headset
28 display of external device
34 headband of headset
36 head fixation part of headset
40 earcup
42 ear cushion
44 earphone housing
46 protrusion in earphone housing for PPG sensor
48 first face of earphone housing
50 second face of earphone housing
72 preauricular skin pit
100 method for determining heart rate data of a user
102 method step of determining a heart rate (HR);
104 method step of determining beat-to-beat (RRi) intervals;
106 method step of determining a heart rate variability (HRV) during a time interval based on the determined beat-to-beat (RRi) intervals;
108 method step of determining low frequency (LF) components and high frequency (HF) components based on the heart rate variability (HRV);
110 method step of determining a baseline measurement of the low frequency (LF) components and the high frequency (HF) components during a first time interval T1, when the user is off-call;
112 method step of measuring a second ratio (LF/HF-on call) between the low frequency (LF) components and the high frequency (HF) components during a second time interval T2, when the user is on-call;
114 method step of detecting stress
502-528 method steps of method for a well-being analysis, such as detecting stress of a user, wearing a headset comprising a PPG sensor
602-640 method steps of a method for a well-being analysis, such as detecting stress of a user, wearing a headset comprising a PPG sensor

The invention claimed is:

1. A system for determining heart rate data of a user, the system comprising a headset for voice communication, the headset being configured to be worn at least partly at or in the ear of a user, the headset comprising:
a voice communication unit for enabling a voice communication call mode for establishing a call between the headset and a far-end device;
a speaker for reproduction of audio signals;
a microphone for reception of audio signals;
a photoplethysmograph (PPG) sensor for optically measuring through the skin of the user in or at the ear of the user;
wherein the headset comprises a processing unit connected to the PPG sensor, where the processing unit is configured for determining heart rate data of the user based on the PPG sensor measurements;
wherein the processing unit is configured for detecting whether the user is on-call with a far-end device or off-call; and
wherein the headset comprises a data communication unit for providing the determined heart rate data of the user, when the user is wearing the headset, for indication of the heart rate data of the user;
wherein the processing unit is configured for determining the heart rate (HR) and determining beat-to-beat (RRi) intervals based on the PPG sensor measurements, and
wherein the processing unit is configured for determining a heart rate varia bility (HRV) during a time interval based on the beat-to-beat (RRi) intervals;
wherein the processing unit is configured for determining low frequency (LF) components and high frequency (HF) components based on the heart rate variability (HRV), where the low frequency (LF) components and the high frequency (HF) components are components in a beat-to beat (RRi) periodogram, where the beat-to beat (RRi) periodogra nn is based on the determined beat-to beat (RRi) intervals;

wherein the processing unit is configured for determining a baseline measurement of the low frequency (LF) components and the high frequency (HF) components during a first time interval Ti, when the user is off-call, and wherein the processing unit is configured for measuring a first ratio (LF/H F-off call) between the low frequency (LF) components and the high frequency (HF) components during the first time interval Ti;

wherein the processing unit is configured for measuring a second ratio (LF/H F-on call) between the low frequency (LF) components and the high frequency (HF) components during a second time interval T2, when the user is on-call; and wherein the processing unit is configured to detect stress by evaluating the second ratio (LF/H F on-call) relative to the first ratio (LF/H F-off call).

2. The system according to claim 1, wherein the headset comprises a notification unit for providing a notification, if the processing unit detects a heart rate increase of the user.

3. The system according to claim 2, further comprising a motion sensor configured for detecting head movements of the user for filtering out motion-induced artefacts in the PPG sensor measurements.

4. The system according to claim 3, further configured such that the PPG sensor is arranged at the preauricular skin pit area of the user for obtaining the PPG signal from the superficial temporary artery, when the user is wearing the headset.

5. The system according to claim 4, further configured such that the PPG sensor is arranged at less than 5 mm over the skin surface, such as less than 4 mm, or such as less than 3 mm, or such as less than 2 mm, or such as less than 1 mm over the skin surface, when the user is wearing the headset.

6. The system according to claim 5, further comprising an earphone housing, and wherein an ear cushion is mounted on the earphone housing, and wherein the PPG sensor is mounted in the earphone housing or in the ear cushion.

7. The system according to claim 6, wherein the earphone housing comprises a protrusion where the PPG sensor is configured to be arranged, such that the protrusion is configured to rest/be situated at the preauricular skin pit area of the user, when the user is wearing the headset.

8. The system according to claim 6, further comprising a fixation part for fixing the position of the earphone housing, when the user is wearing the headset, such that the PPG sensor is arranged at the preauricular skin pit area of the user.

* * * * *